United States Patent [19]
Takami et al.

[11] Patent Number: 4,620,437
[45] Date of Patent: Nov. 4, 1986

[54] GAS SENSOR

[75] Inventors: Akio Takami; Toshitaka Matsuura; Toshifumi Sekiya; Yoshiaki Kuroki, all of Nagoya, Japan

[73] Assignee: NGK Spark Plug Co., Ltd., Nagoya, Japan

[21] Appl. No.: 726,369

[22] Filed: Apr. 23, 1985

[30] Foreign Application Priority Data

Apr. 25, 1984 [JP] Japan .................... 59-83379

[51] Int. Cl.$^4$ ............................................. G01N 27/12
[52] U.S. Cl. ............................................. 73/23; 338/34
[58] Field of Search .............. 73/23, 27 R; 338/34; 422/98; 340/634

[56] References Cited

U.S. PATENT DOCUMENTS 4,413,502 11/1983 Ohta et al. ........................ 73/23
4,535,316 8/1985 Wertheimer et al. ............. 73/23

Primary Examiner—Stephen A. Kreitman
Attorney, Agent, or Firm—Fleit, Jacobson, Cohn & Price

[57] ABSTRACT

A gas sensor has a heater circuit with a voltage-dividing element, and a voltage to energize the heater circuit is applied through a resistive lead wire element, while a sensor voltage to measure the resistance of a gas-sensitive element is branched from the heater circuit.

2 Claims, 10 Drawing Figures

GAS SENSOR

BACKGROUND OF THE INVENTION

1. Field of the Invention

This invention relates to a gas sensor, and more particularly to a gas sensor having a heater to warm up a gas-sensitive element thereof.

2. Description of the Prior Art

In general, there are two types of gas sensors, i.e., contact-combustion type and semiconductor type.

The contact-combustion type gas sensor is made by depositing catalyst on the surface of a platinum wire. When a gas comes in contact with the catalyst, reaction (combustion) heat generated by such contact results in a temperature rise of the platinum wire. The change in the electric resistance of the platinum wire due to the temperature rise is measured to determine the presence or concentration of the gas.

The semiconductor type gas sensor uses those semiconductors whose electric resistance changes when a gas comes in contact with them, and such resistance change enables determination of the presence or concentration of the gas. Various oxide semiconductors, such as tin oxide ($SnO_2$), zinc oxide (ZnO), titanium oxide ($TiO_2$), and cobalt oxide (CoO), are used to make gas sensors for various purposes while selecting suitable operating temperature and kind of catalyst to be carried thereby for each specific purpose. Examples of the oxide smiconductor gas sensors are propane gas sensors, carbon monoxide (CO) sensors, oxygen ($O_2$) sensors, and humidity sensors.

Built-in heaters are often provided in such gas sensors for various purposes, such as for burning off contaminants precipitated on their surface, for preventing deposition of contaminants, and for enhancing the acitivity of their gas-sensing elements.

To detect any change in the resistance of the gas-sensing elements, it has been practiced as a convenient method to apply a known constant voltage thereto from the outside. With the constant voltage, the resistance change is reflected in a change of current therethrough, and the current change may be detected as a voltage change across a comparison resistor through which the current flows.

The voltage for the resistance change detection is not necessarily the same as that for the heater, so that gas sensors of the prior art have a shortcoming in that two separate power sources are necessary, one for the heaters and one for the resistance change detection. The need of two power sources tends to increase the manufacturing cost of the gas sensor.

For instance, oxygen sensors are used to keep automobile engine exhaust gas clean. More specifically, an oxygen sensor is used to determine whether the air-fuel ratio in the composition of automobile engine exhaust gas is above or below the theoretical optimal value. A typical oxygen detector for this purpose detects resistance change in an oxide semiconductor element, such as an element made of titanium oxide ($TiO_2$), cobalt oxide (CoO), and tin oxide ($SnO_2$). The sensor output (in the form of electric signal) is fed back to an engine control system so as to keep the engine exhaust gas composition in a narrow range around the theoretical optimal air-fuel-ratio which range is suitable for efficient action of ternary or other catalyst therein. In this case, it has been considered preferable to provide a heater in the oxygen sensor because the sensor operation is unstable for low temperature exhaust gas below 400° C. such as that from cold engine.

As to the power source for such heater, a car battery rated at 6 V or 12 V is convenient and desirable from the standpoint of heater design. On the other hand, as to the power source for the oxygen sensor to detect the resistance change of its gas-sensitive element, a lower voltage of 1–5 V is desirable from the standpoint of gas sensor durability. Thus, two kinds of power sources are necessary in this case.

The conventional gas-sensitive element which detects resistance change thereof has another shortcoming in that the resistance value of the gas-sensitive element itself is affected by temperature. Thus, the measured value of the resistance change involves both a temperature depending portion and a gas concentration depending portion. When such gas-sensitive element is used over a wide temperature range, its accuracy of detection is inevitably low. To minimize the temperature influence, a temperature compensating element may be used in conjunction with the gas-sensitive element, but such compensating element causes an increase in the gas sensor cost.

SUMMARY OF THE INVENTION

Therefore, an object of the invention is to obviate the above-mentioned shortcomings of the prior art by providing an improved gas sensor having an excellent low-temperature activity. To this end, a gas sensor according to the invention uses the combination of a gas-sensitive element, a ceramic heater, and a resistive lead wire element, said ceramic heater being formed on a ceramic substrate by that metallizing techniques which has been developed and disclosed before by the inventors.

In an embodiment of the gas sensor of the invention, the ceramic heater can be made by overlaying an alumina green tape (a flexible tape made of a mixture of alumina and organic resin) carrying a heater pattern onto a tubular alumina ceramic body, and sintering them at a high temperature in a reducing atmosphere, as disclosd in the inventors' Japanese Patent Application No. 86,868/1976. The above heater pattern is formed by printing a tungsten-base heater pattern on the alumina green tape by conventional thick-film metallizing techniques.

Another embodiment of the gas sensor of the invention can be produced by overlaying a thick-film gas-sensitive element on a planar alumina ceramic substrate carrying a heater pattern printed thereon through the platinum metallizing method, which substrate has been disclosed in the inventors' Japanese Patent Application No. 225,561/1983.

In either of the above embodiments of the gas sensor of the invention, the heater pattern on the alumina green tape or the planar alumina ceramic substrate is made in the form of a serial circuit having a heat-generating portion and a voltage-dividing portion. The voltage-dividing portion is preferably resistive. The voltage to drive the heater pattern is applied through a resistive lead wire element. The voltage for measuring the resistance of a gas-sensitive element representing the gas concentration is taken from the boundary between the heat-generating portion and the voltage-dividing resistance portion. Whereby, both the gas sensing function and the heating function are fulfilled by using only one power source while minimizing the temperature dependency of the gas sensing function.

A preferred embodiment of the gas sensor according to the invention has a ceramic substrate carrying a linear heater circuit with a first terminal and a second terminal at opposite ends thereof, which heater circuit has a heat-generating portion and a voltage-dividing portion connected to the above second terminal. A gas-sensitive element is disposed on the substrate in juxtaposition to the heat-generating portion. The gas-sensitive element has a first electrode and a second electrode buried therein with a spacing between the two electrodes. The first electrode is connected to a third terminal on said substrate, and the second electrode is connected to the boundary between the heat-generating portion and the voltage-dividing portion of the heater circuit. Finally, the gas sensor has, as an essential part thereof, a resistive lead wire element connected to the second terminal.

The resistance of such resistive lead wire element connected to the second terminal is such that a heater voltage across the resistive lead wire element and the linear heater circuit is divided so as to provide a suitable sensor voltage at the above-mentioned boundary for measuring resistance of said gas-sensitive element.

BRIEF DESCRIPTION OF THE DRAWINGS

For a better understanding of the invention, reference is made to the accompanying drawings, in which.

Throughout different views of the drawings, 1 is a ceramic carrier board, 3 is a metallic body, 5 is a protector, 9 is filler powder, 11 is a glass seal, 13a and 13c are non-resistive lead wires, 13b is a resistive lead wire element, 15 is a silicone rubber plug, 17 is an outer shell, 21 is a first green sheet, 23 is a second green sheet, 25 is a heat-generating portion of a heater circuit, 27 is a first electrode, 29 is a second electrode, 31 is a voltage-dividing portion of the heater circuit, 35a, 35b, 35c are first, second, third connecting portions, 37 is a window, 41 is a gas-sensitive element, $R_H$ is the resistance of the heat-generating portion 25, $R_1$ is the resistance of the voltage-dividing portion 31, $R_2$ is the resistance of the resistive lead wire element 13b, $R_T$ is the resistance of the gas-sensitive element 41, and BAT is a battery as an electric power source.

DESCRIPTION OF THE PREFERRED EMBODIMENTS

Figure 1:
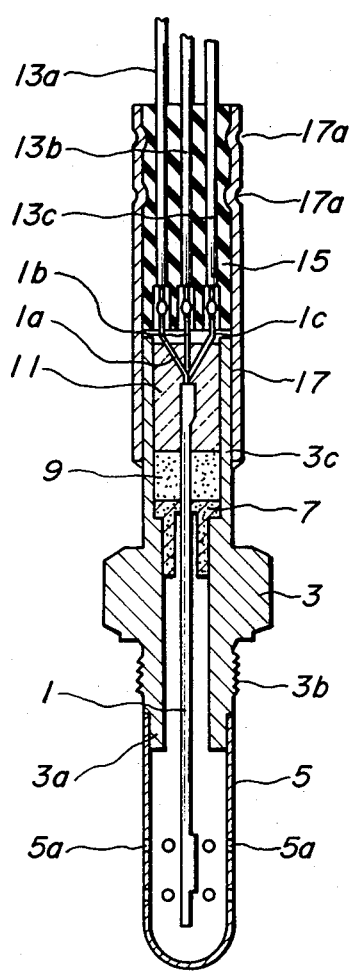
FIG. 1 is a vertical sectional view of the essential portion of a gas sensor according to the present invention.

The invention will be described in detail now by referring to a preferred embodiment illustrated in the accompanying drawings. FIG. 1 shows a vertical sectional view of a gas sensor with a heater according to the invention, which gas sensor is suitable for detecting oxygen concentration in exhaust gas from any of various combustion apparatuses such as car engines.

Referring to FIG. 1, a ceramic carrier board 1 carries a gas-sensitive element and a heater circuit as will be described hereinafter. The ceramic carrier board 1 is secured to the inside of a cylindrical metallic body 3, so that the body 3 facilitates the mounting of the gas sensor of the invention on a combustion apparatus whose gas concentration is to be checked. To protect the gas-sensitive element carried by the ceramic carrier board 1, a porous cover 5 with a number of through-holes 5a is mounted on the lower end or the combustion apparatus side end 3a of the metallic body 3. Male threads 3b are formed on the outer surface of the metallic body 3, so as to screw the gas sensor of the invention onto the combustion apparatus. The ceramic carrier board 1 is spaced from the wall of the metallic body 3 by a spacer 7, but the board 1 is gastightly secured to the metallic body 3 by the combination of a layer of filler powder 9 and a glass seal 11.

The filler powder 9 may, for instance, be a mixture consisting of talc and glass particles at 1:1 ratio. The glass seal 11 is, for instance, formed at 600° C. by sealingly filling the gap between the ceramic carrier board 1 and the metallic body 3 with low-melting-point glass. The glass seal 11 prevents gas being measured from leaking and firmly holds three terminal strips 1a, 1b, and 1c emanating from the ceramic carrier board 1. The terminal strips 1a and 1c from the board 1 are connected to non-resistive lead wires 13a and 13c by brazing respectively, while the terminal strip 1b is connected to a resistive lead wire element 13b by brazing. Whereby, an input voltage is applied to the board 1 through the non-resistive lead wire 13a and the resistive lead wire element 13b while an output detection signal is extracted from the board 1 through the non-resistive lead wire 13c, as will be explained in detail hereinafter.

A silicone rubber plug 15 is applied to the outer end of an outer shell 17, while the inner end of the outer shell 17 is joined to the metallic body 3 by brazing. The plug 15 is tightly fastened to the outer shell 17 by pressing the outer shell 17 inwardly as shown by dents 17a of FIG. 1. Whereby, the plug 15 insulates and protects the joints of the terminal strips 1a, 1c, and 1b with the corresponding non-resistive lead wires 13a, 13c, and the resistive lead wire element 13b, and prevents oil and water from seeping into the gas sensor.

FIG. 2A through FIG. 2E show how a test specimen of the ceramic carrier board 1 was produced. A 1 mm thick first ceramic board 21 and a 0.2 mm thick second ceramic board 23 were made by the following steps; namely, preparing a powder mixture consisting of 100 parts by weight of oxide powder with a mean particle diameter of 1.5 μm containing 92% by weight of alumina ($Al_2O_3$), 4% by weight of silica ($SiO_2$), 2% by weight of calcia (CaO), and 2% by weight of magnesia (MgO), 12 parts by weight of butyral resin, and 6 parts by weight of dibutyl phthalate; making a slurry by mixing the thus prepared powder mixture in an organic solvent; and shaping the green sheets from the slurry by using a doctor plate.

Figure 2:
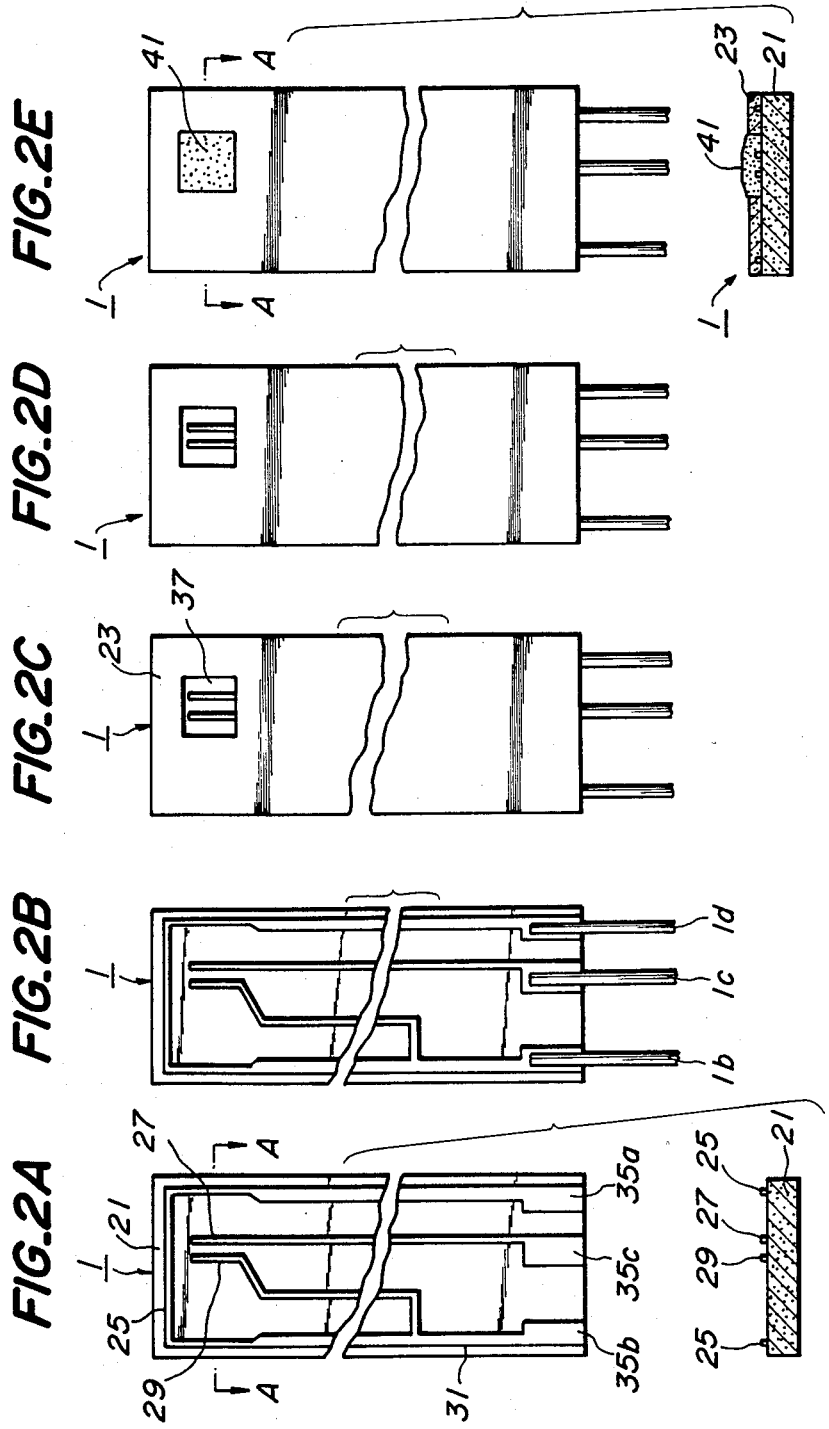
FIG. 2A through FIG. 2E are diagrammatic illustrations showing different stages of a process for producing the gas sensor of the invention.

Referring to FIG. 2A, a heater circuit having a heat-generating portion 25 and a voltage-dividing portion 31 serially connected to the heat-generating portion 25 was formed on the first ceramic green sheet 21. A first connecting portion 35a and a second connecting portion 35b were provided at opposite ends of the heater circuit in such a manner that the second connecting portion 35b was at the free end of the voltage-dividing portion 31. A first electrode 27 of a gas-sensitive element 41 (FIG. 2E) was formed on the first green sheet 21 while providing a third connecting portion 35c electrically connected to the first electrode 27. A second electrode 29 of the gas-sensitive element 41 was formed on the first green sheet 21 so as to face the first electrode 27 with a spacing therefrom, and the second electrode 29 was connected to the boundary between the heat-generating portion 25 and the voltage-dividing portion 31 of the heater circuit.

Both the heater circuit having the heat-generating portion 25 and the voltage-dividing portion 31 and the circuits of the first and second electrodes 27, 29 were printed as thick-film patterns by using a platinum paste containing 7% of alumina ($Al_2O_3$) based on the platinum (Pt) content therein. The first electrode 27 joined to the third connecting portion 35c was used as an output extracting circuit pattern. The second electrode 29 joined to the above-mentioned boundary was used as a divided-voltage extracting circuit pattern.

Terminal strips 1a, 1b, and 1c, for instance in the form of short platinum wires, were bonded to the connecting portions 35a, 35b, and 35c respectively, as shown in FIG. 2B. The second green sheet 23 with a punched window 37 was overlaid on and bonded to the first green sheet 21 by pressing at a high temperature, so that the heater circuit and the electrode circuits were sandwiched between the two green sheets 21 and 23, as shown in FIG. 2C. The size and the position of the punched window 37 were such that the tip portions of the two electrodes 27 and 29 were exposed to the outside therethrough. The green sheets 21 and 23 thus bonded were sintered at 1,500° C. for two hours in air, and an interim product of the ceramic carrier board 1 was made, as shown in FIG. 2D.

Referring to FIG. 2E, a gas-sensing element 41 was then formed in the window 37, so that a final product of the ceramic carrier board 1 was completed. To form the gas-sensitive element 41, a titania ($TiO_2$) paste was made by preparing a mixture consisting of 100 parts by mole of titania powder with a mean particle diameter 1.2 $\mu$m, 1 part by mole of platinum black powder, and 3% by weight of ethyl cellulose based on the total amount of titania and platinum black powder; and kneading the mixture in BUTYCARUBITOL while adjusting the viscosity of the paste at 300 poise. The titania paste was printed as a thick film filling the window 37, while ensuring tight contact of the thick film with the tip portions of the first and second electrodes 27 and 29. The gas-sensitive element 41 was completed by sintering the above thick film at 1,200° C. for one hour in air.

A resistive lead wire element 13b, formed of meshed stainless steel fine wires, was brazed to the terminal strip 1b bonded to the second connecting portion 35b of the thus prepared ceramic carrier board 1. Non-resistive lead wires 13a and 13c, formed of copper fine wires (nickel plated), were brazed to the remaining terminal strips 1a and 1c respectively.

The inventors have carried out tests on both the specimen of the invention thus produced and a reference gas sensor of the prior art.

Figure 3:
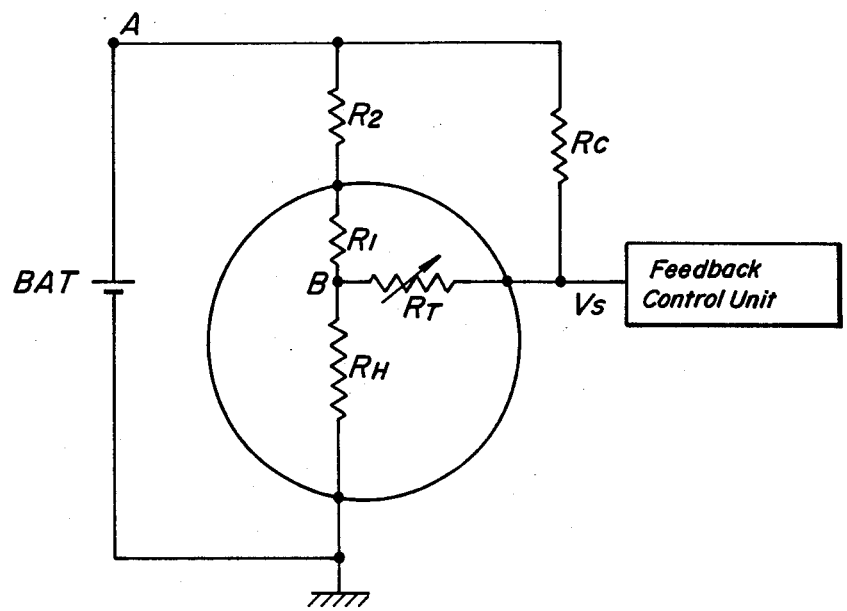
FIG. 3 is a circuit diagram showing an equivalent circuit of an arrangement for detecting gas concentration by using either a gas sensor according to the invention or a reference gas sensor.

An equivalent circuit of the gas sensor according to the invention is shown in FIG. 3. The resistance $R_2$ of the resistive lead wire element 13b is serially connected to the resistance $R_1$ of the voltage-dividing portion 31 which is in series with the resistance $R_H$ of the heat-generating portion 25. One end of the resistance $R_T$ of the gas-sensitive element 41 is connected to the boundary between the heat-generating portion resistance $R_H$ and the voltage-dividing portion resistance $R_1$. The free end of the gas-sensitive element resistance $R_T$ is brought to the outside of the gas sensor and connected to a feedback control unit which is out of the scope of the invention. The free end of the heat-generating portion resistance $R_H$ is grounded. A power source battery BAT is connected across the ground and the free end of the resistive lead wire element resistance $R_2$. The free end of the gas-sensitive element resistance $R_T$ is connected to the free end of the resistive lead wire element resistance $R_2$ through a constant comparison resistance $R_C$ outside the gas sensor.

Lead wires for a reference gas sensor were all made of copper wires. Table 1 shows the numerical values of the heat-generating portion resistance $R_H$, the voltage-dividing portion resistance $R_1$, and the resistive lead wire element resistance $R_2$ which were used in the tests.

TABLE 1

Unit: ohms (Ω)

| Item* | Resistance value | |
|---|---|---|
| | Sensor of invention | Reference sensor |
| $R_H$ | 6.2 | 6.2 |
| $R_1$ | 0.4 | 0.8 |
| $R_2$ | 0.6 | below 0.01 |

Figure 4:
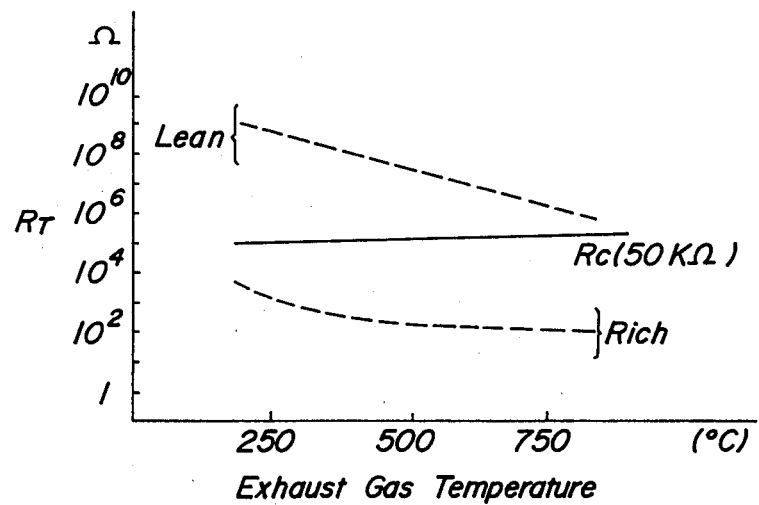
FIG. 4 is a graph showing the resistance vs. exhaust gas temperature characteristics for the gas-sensitive element used in both the gas sensor of the invention and the reference gas sensor.

*$R_H$: Heat-generating portion resistance
$R_1$: Voltage-dividing portion resistance
$R_2$: Resistance of an about 30 cm long resistive lead wire element FIG. 4 shows the gas-sensitive element (titania element) resistance $R_T$ vs. exhaust gas temperature characteristics of the gas sensors tested for a lean exhaust gas and a rich exhaust gas.

Figure 5:
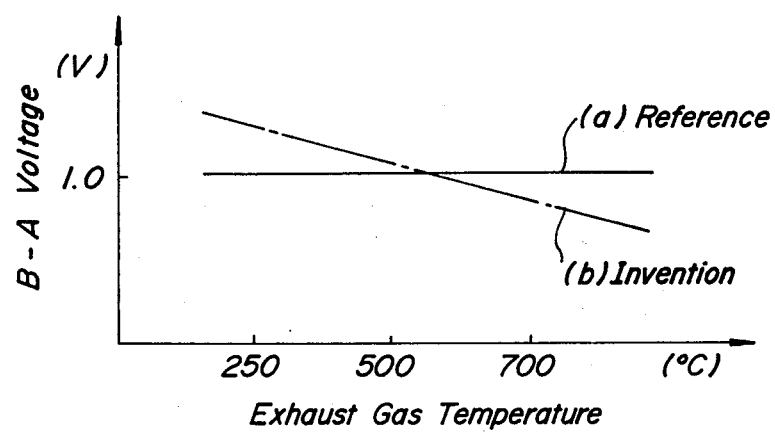
FIG. 5 is a graph showing the variation of the voltage across the points A and B of FIG. 3 at different exhaust gas temperatures for both the gas sensor of the invention and the reference gas sensor.

The specimen gas sensor of the invention and the reference gas sensor were connected to a feedback control system driven by an oxygen sensor for an engine of 2 1 displacement with electronic-fuel-injection (EFI) control. The power source battery BAT used in the tests had an output voltage of 14 V. FIG. 5 shows B-A voltages across the point A at the output of the battery BAT and the point B at the boundary between the heat-generating portion 25 and the voltage-dividing portion 31 as depicted in FIG. 3. In the case of the reference gas sensor, an A-B voltage of about 1 V existed regardless of the exhaust gas temperature as shown by the curve (a) of FIG. 5.

When the exhaust gas temperature was 250° C., the output voltage $V_S$ from the gas sensor of the invention was about 0.8 V for the rich exhaust gas and about 0 V for the lean exhaust gas. Thus, the gas sensor of the invention proved to produce satisfactory output voltage. As the temperature of the exhaust gas increased, the output voltage $V_S$ for the rich exhaust gas somewhat increased to about 0.9 V while that for the lean exhaust gas also increased. When the exhaust gas was 800° C., the output voltage from the gas sensor of the invention for the lean exhaust gas increased to about 0.4

V and the operating range shrank slightly, but it proved to be still sufficient for all practical purposes. The output voltages from the gas sensor of the invention as measured in the tests are shown by solid line curves (b) in FIG. 6, while those from the reference gas sensor are shown by chain line curves (a) thereof.

In the case of the above-mentioned reference gas sensor, when the exhaust gas temperature was high, its output for lean exhaust gas was high. The reason for it is in that, as shown in FIG. 4, when the exhaust gas temperature is high, the gas-sensitive element resistance $R_T$ for the lean exhaust gas (broken line of FIG. 4) is low as compared with the constant comparison resistance $R_C$ of 50 kΩ (solid line of FIG. 4), and since the sensor output depends on the ratio between the reference resistance (the constant resistance $R_C$) and the gas-sensitive element resistance, i.e., the ratio (reference resistance)/(total resistance), the output for the lean exhaust gas becomes high. The gas-sensitive element resistance for rich discharge gas increased rapidly as the temperature of the exhaust gas decreased, as shown by the broken line curve of FIG. 4. This is due to rapid reduction of the gas-sensitivity of the element with the temperature reduction. Thus, the gas sensor output for rich exhaust gas drops at 250° C.

Figure 6:
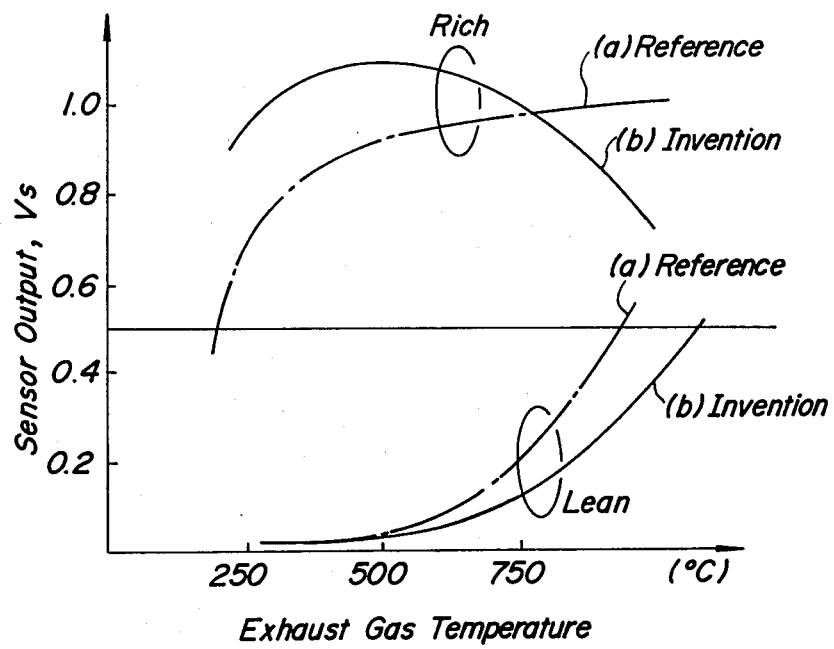
FIG. 6 is a graph showing the gas sensor output vs. exhaust gas temperature characteristics for both the gas sensor of the invention and the reference gas sensor.

The B-A voltage drop of the specimen gas sensor of the invention was as shown by the chain line curve of FIG. 5. In operation of the feedback control unit with the gas sensor connected thereto, the gas sensor output is compared against a preset reference level as shown in FIG. 6, so that control signals are produced depending on whether the gas sensor output is above or below the reference level. As can be seen from FIG. 6, the gas sensor of the invention can operate over a wider temperature range than the reference gas sensor can do.

The reason why the gas sensor of the invention can operate over a wider temperature range is as follows. As the battery BAT is connected to the gas sensor, heat is generated at the heat-generating portion resistance $R_H$. Since the heater circuit including the heat-generating portion is made of platinum (Pt) having a positive temperature coefficient of resistance, the resistance $R_H$ increases with the heat generation thereat. At the same time, the voltage-dividing portion resistance $R_1$, which is an extension of the heat-generating portion resistance $R_H$ on a common ceramic substrate, is also heated, and the resistance $R_1$ also increases with the increase of the resistance $R_H$. The B-A voltage for driving the gas-sensitive element 41 depends on the ratio.

$$(R_1+R_2)/(R_1+R_2+R_H),$$

and in the case of the reference gas sensor the lead wire resistance is negligible, i.e., $R_2 \cong 0$, so that no significant change occurs in the above ratio when the resistances $R_1$ and $R_H$ increase or decrease simultaneously. Thus, the B-A voltage in the reference gas sensor is substantially constant even when the exhaust gas temperature varies as shown by the solid line curve (a) of FIG. 5.

On the other hand, in the gas sensor of the invention, the resistance $R_2$ of the resistive lead wire element 13b has a finite value and is disposed in the outside of the gas sensor, so that the ohmic value of the resistance $R_2$ is hardly affected by the temperature at the tip of the gas sensor and is held substantially at a constant level even when the temperature in the gas sensor varies. Thus, the A-B voltage of the gas sensor of the invention decreases with the increase of the exhaust gas temperature as shown by the chain line curve (b) of FIG. 5, because the resistances $R_1$ and $R_H$ increases with their temperature rise while the resistance $R_2$ remains constant regardless of temperature change in the gas sensor.

Accordingly, with the gas sensor of the invention, the synergistic effect of the curves of FIG. 4 and the chain curve (b) of FIG. 5 is achieved, and the output $V_S$ from the gas sensor of the invention becomes as shown by the solid line curves (b) of FIG. 6 and ensures satisfactory operation over a wide temperature range.

The resistance $R_2$ in series with the voltage-dividing portion resistance $R_1$ may be provided by a fixed resistor disposed in the feedback control unit, but from the standpoint of allowing heat dissipation and avoiding localized heat generation, the use of the resistive lead wire element 13b having the resistance $R_2$ is preferable.

In the specimen described above, a planar ceramic board with circuit patterns formed by metallizing platinum is used, but the ceramic substrate can be cylindrical or of other suitable shape and the circuit patterns can be formed by metallizing tungsten or other suitable metallic material.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A gas sensor, comprising a ceramic substrate; a heater circuit with a first terminal and a second terminal at opposite ends thereof, said heater circuit being mounted on said substrate and having a heat-generating portion and a voltage-dividing portion connected to said second terminal; a gas-sensitive element disposed on said substrate in juxtaposition to said heat-generating portion; a first electrode and a second electrode buried in said gas-sensitive element with a spacing therebetween, said first electrode connected to a third terminal on said substrate, said second electrode connected to boundary between said heat-generating portion and said voltage-dividing portion; and a resistive lead wire element connected to said second terminal, resistance of said resistive lead wire element being such that a heater voltage across said resistive lead wire element and said heater circuit is divided so as to provide a suitable sensor voltage at said boundary for measuring resistance of said gas-sensitive element.

2. A gas sensor as set forth in claim 1, wherein said ceramic substrate has a first ceramic sheet and a second ceramic sheet with a window, said first and second sheets being overlaid one over the other while sandwiching said heater circuit and said electrodes therebetween, and said gas-sensitive element is formed so as to cover said window of said second sheet and bury tip portions of said first and second electrodes in the gas-sensitive element.

* * * * *